(12) United States Patent  (10) Patent No.: US 9,151,742 B2
Chen  (45) Date of Patent: Oct. 6, 2015

(54) HAND-HELD MEDICAL DEVICE

(71) Applicant: Roche Diagnostics Operations, Inc., Indianapolis, IN (US)

(72) Inventor: Ming-Wen Chen, Taipei (TW)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 13/944,132

(22) Filed: Jul. 17, 2013

(65) Prior Publication Data

US 2013/0302221 A1  Nov. 14, 2013

Related U.S. Application Data

(63) Continuation of application No. PCT/EP2012/050550, filed on Jan. 16, 2012.

(30) Foreign Application Priority Data

Jan. 19, 2011  (EP) .................... 11151427

(51) Int. Cl.
G01N 33/50 (2006.01)
A61B 5/145 (2006.01)
G01N 33/487 (2006.01)

(52) U.S. Cl.
CPC ............ *G01N 33/50* (2013.01); *A61B 5/14532* (2013.01); *G01N 33/48764* (2013.01); *A61B 2562/0295* (2013.01)

(58) Field of Classification Search
CPC ............................ G01N 33/50; A61B 5/14532
See application file for complete search history.

(56) References Cited

U.S. PATENT DOCUMENTS

| 2008/0103415 A1 | 5/2008 | Roe et al. |
| 2010/0216246 A1 | 8/2010 | Konya et al. |
| 2012/0178152 A1* | 7/2012 | Eisenhardt et al. ........ 435/288.7 |

FOREIGN PATENT DOCUMENTS

| EP | 2279689 A1 | 2/2011 |
| WO | 2006/000792 A1 | 1/2006 |
| WO | 2008/043565 A3 | 4/2008 |
| WO | 2010/046323 A1 | 4/2010 |

* cited by examiner

*Primary Examiner* — Sam P Siefke
(74) *Attorney, Agent, or Firm* — Roche Diabetes Care, Inc.

(57) ABSTRACT

Disclosed herein are hand-held medical devices, such as blood glucose meters, that include a housing with a cassette compartment for receiving an exchangeable test tape cassette, a drive assembly comprising an electric motor and a gear arrangement adapted for rotating a tape spool of the test tape cassette, where the gear arrangement has a worm drive in which a worm meshes with a worm wheel and a multistage speed-reducing unit comprising a plurality of spur gears arranged between the worm wheel and an output gear that can be directly coupled to the tape spool.

23 Claims, 2 Drawing Sheets

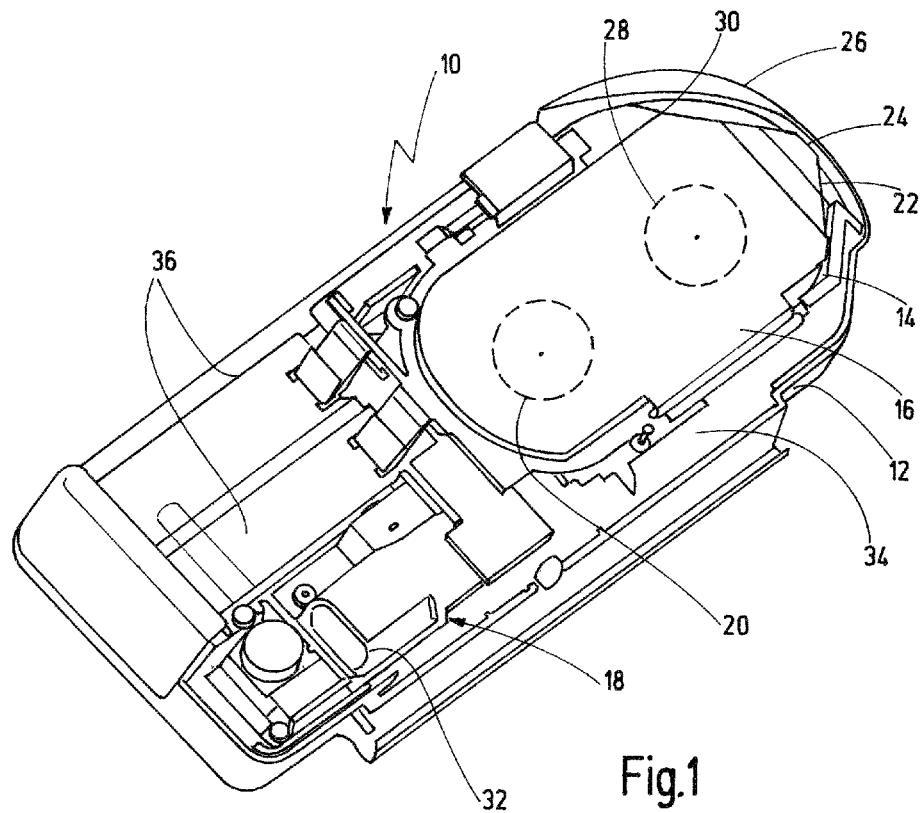
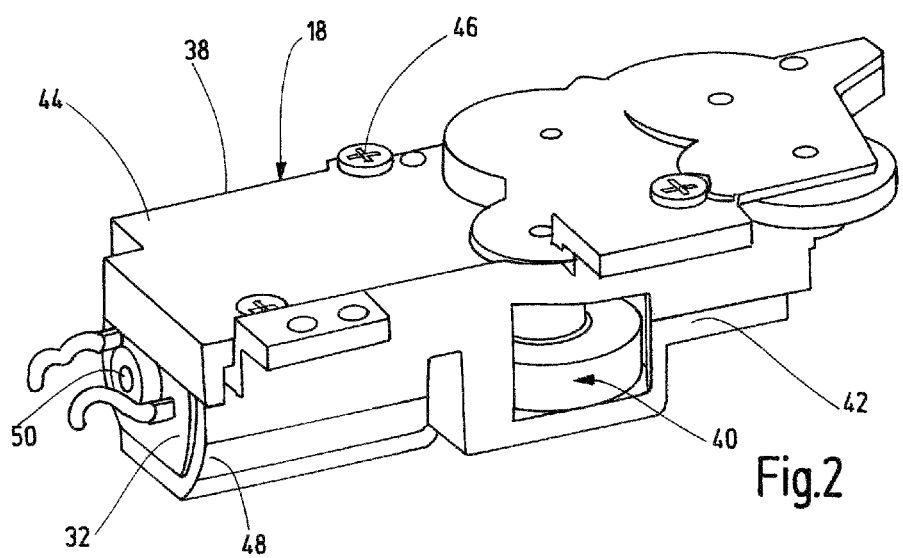

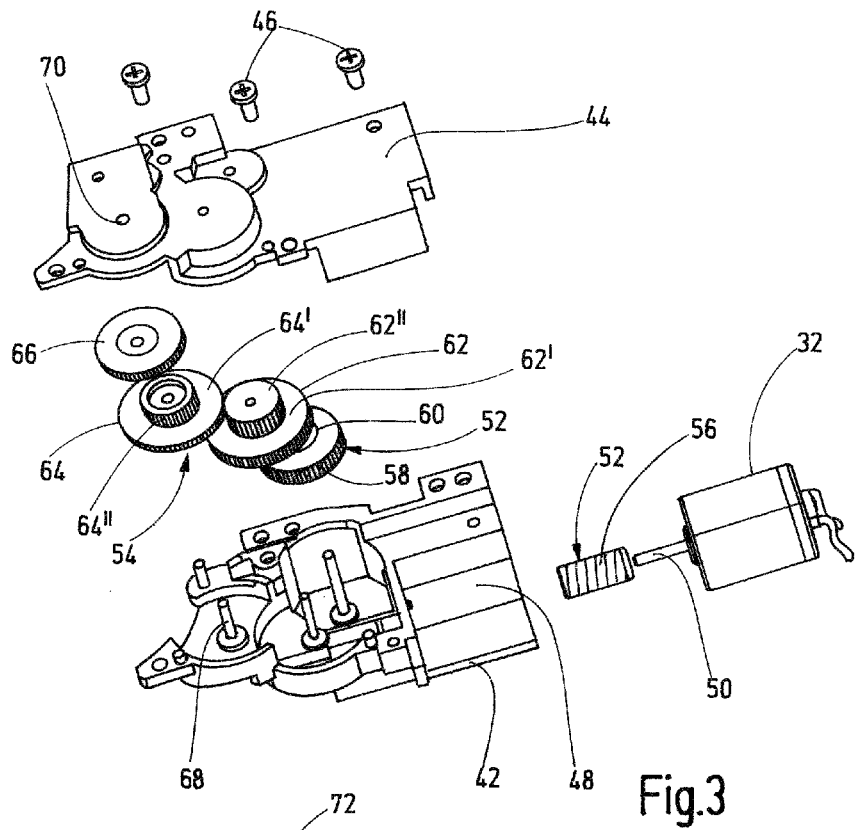
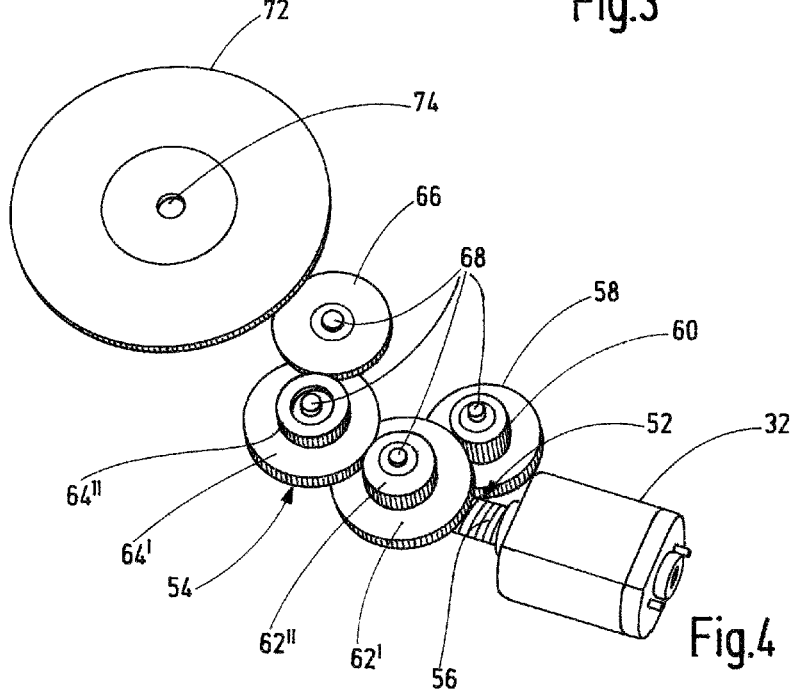

HAND-HELD MEDICAL DEVICE

CROSS-REFERENCE TO RELATED APPLICATIONS

This patent application is a continuation of Int'l Patent Application No. PCT/EP2012/050550; filed 16 Jan. 2012, which claims the benefit of EP Patent Application No. 11151427.9; filed 19 Jan. 2011. Each patent application is incorporated herein by reference as if set forth in its entirety.

TECHNICAL FIELD

The invention relates generally to hand-held medical devices, in particular blood glucose meters, and more particularly to such devices that have a housing with a cassette compartment, an exchangeable test tape cassette received in the cassette compartment and a drive assembly comprising an electric motor and a gear arrangement adapted for rotating a tape spool of the test tape cassette, such that a test tape of the test tape cassette can be wound forwards and test elements thereon can be provided for successive use.

BACKGROUND

Hand-held medical devices are used in practice as, for example, blood glucose meters for self-monitoring by diabetics. A plurality of test fields is provided on a spoolable test tape in the tape cassette. The reactive test fields are examined photometrically after application of a small amount of blood sample to determine the glucose content as exactly and reliably as possible. Such tape cassettes are intended to be inserted as a disposable part into a compact hand-held device housing to allow the necessary analytical steps to be carried out automatically and rapidly. In addition to a reliable positioning of the test elements, it also is necessary for practical purposes to ensure that their on-the-spot use is not impaired by excessive noise development. In this context, Intl Patent Application Publication No. WO 2010/046323 proposes using a compact high-speed motor in combination with a reduction gear unit.

On this basis, an object is to further improve known test devices and to achieve a reliable test element positioning with little interfering noise in a compact construction.

BRIEF SUMMARY

Hand-held medical devices are disclosed that use a worm drive and subsequent spur gears to reduce size and to control the rotational movement precisely. Accordingly, it is proposed that the gear arrangement has a worm drive in which a worm meshes with a worm wheel and a multistage speed-reducing unit downstream of the worm drive and comprises a plurality of spur gears arranged between the worm wheel and an output gear that can be directly coupled to a tape spool. Preferably, the worm is directly mounted on the motor shaft. This combination allows one to considerably reduce size and operational noise, while at the same time ensures a sufficient turning movement for the rotation of the tape spool. Specifically, a high gear ratio can be performed in a small construction space, and the transmission can be kept non-reversible and with low backlash.

In one embodiment, the device includes a speed-reducing unit that has at least two, preferably three, meshing gear pairs for reducing rotational speed between the worm drive and the output gear. In another embodiment, the speed-reducing unit provides a speed-reduction ratio between the rotational speed of the electric motor and the output gear that is more than about 300, more than about 400, or alternatively in a range between about 400 to about 500. Such a gear ratio surprisingly has been found to provide an optimum for several boundary conditions that are critical for the device design. Particularly, size reduction and elimination of noise, as well as sufficient output torque, in combination with a small-power direct current (DC) motor are important for such a hand-held medical device.

To further attenuate operational noise, each of the spur gears can have at least about 10 to at least about 14 teeth. Likewise, the output gear can provide a torque on the tape spool of more than about 20 mNm to about 50 mNm. This design permits reliable tape transport even through shielding seals, while at the same time avoiding an unwanted straining of the tape.

In another embodiment, the device includes an exchangeable tape cassette having a first tape spool for unused tape, a second tape spool for used tape, and a seal through which the test tape is transported between the spools, where the output gear acts on the second spool. In this manner, a large number of tests can be stored on the tape without the user having to handle waste material.

An improvement in safe and reliable handling can be achieved when the worm drive is self-locking, such that the worm gear cannot drive the worm when a reverse torque is exerted on the tape spool. In this context, the self-locking force of torque of the worm drive is greater than about 10 mNm and alternatively greater than about 14 mNm.

To achieve a compact configuration, rotational axes of the spur gears are parallel to a rotational axis of the tape spool. Likewise, the rotational axis of the electric motor is skewed or perpendicular to the rotational axes of the spur gears. For a further reduction of the total constructional dimensions, the spur gears can include overlapping pairs of stepped wheels, where the spur gears can be arranged in a non-linear configuration, and where the centers of the spur gears span a polygon such as a triangle or quadrangle.

A further manufacturing simplification and constructional improvement can be achieved when the drive assembly is mounted between a top-cover and a bottom-cover of a gearbox. It also is beneficial when the axes of the spur gears extend from the bottom-cover to the top-cover of the gearbox, and the shaft of the electric motor lies horizontally between the covers. For further improvement of the assembly, the top-cover and bottom-cover of the gearbox are detachably connected together by means of, for example, screws.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 1 shows a top view of a cassette-type blood glucose meter illustrated with the cover removed and showing the location of a cassette drive assembly.

FIG. 2 is an expanded perspective view of the cassette drive assembly.

FIG. 3 is an exploded view of the cassette drive assembly.

FIG. 4 is a top view of the cassette drive assembly with the covers removed and illustrating a worm drive in combination with a speed-reducing spur gear unit.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The devices now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the devices described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

The drawings show a medical device configured as a portable blood glucose meter 10 for self-monitoring of blood glucose and comprising a housing 12 with a cassette compartment 14, a disposable tape cassette 16 replaceably loaded in the cassette compartment and a drive assembly 18 for rotating a tape spool 20 of the tape cassette 16, such that an analytical test tape 22 of the cassette can be wound forward and reactive test fields thereon can be provided at an application tip 24 for application and investigation of a blood sample. On-board photometric detection of the analyte is known per se in the state of the art and needs not to be explained in further detail.

Devices

FIG. 1 shows an embodiment of a glucose meter 10 from the broad side with a housing cover removed. A housing opening for sample application is shown closed by a moveable protective cover 26. The tape spool 20 is intended for winding-on the used section of the test tape 22, whereas a tape spool 28 for unused tape is shielded in a chamber closed by a seal 30 which allows the tape to be pulled there through. The drive assembly 18 is adapted to ensure a reliable tape transport through the seal 30, while extensively reducing the necessary installation space and the operating noise. For such purposes, the drive assembly 18 comprises a high-speed DC micro motor 32 that can be energized via a control logic on a circuit board 34 in connection with a power supply such as batteries 36.

FIG. 2 shows that the drive assembly 18 comprising a gearbox 38, the DC motor 32, and a subsequent gear arrangement 40 adapted for reducing the rotational speed and correspondingly increasing torque to provide an adequate rotation of the tape spool 20. The gearbox 38 includes a bottom cover 42 and a top cover 44 secured to the bottom cover via screws 46. The bottom cover 42 forms a chamber 48 for housing the DC motor 32 in an orientation where the motor shaft 50 lies horizontally between the covers 42, 44. In this manner, the total height is reduced, and the assembly becomes compact.

FIG. 3 shows an exploded view that further elucidates the gear arrangement 40, which includes a worm drive 52 and a multistage speed-reducing transmission unit 54.

The worm drive 52 includes a worm 56 in the form of a cylindrical screw and a worm wheel 58. In the assembled state, the worm 56 can be mounted on the motor shaft 50 such that it meshes with the worm wheel 58 at 90°. The axis of the helical worm 56, and respectively the motor shaft 50, is neither parallel nor intersecting with the axis of the worm wheel 58. The transmission unit 54 comprises a plurality of spur gears 60,62,64,66 in the drive train following the worm wheel 58 and forming three meshing gear pairs for a reduced gear ratio. The spur gears 62,64 comprise stepped wheels with a large and a small diameter toothed wheel 62',62" and 64',64" in a coaxial configuration. For supporting the spur gears 60,62,64,66, the bottom cover 42 has four upstanding axle journals 68 that are parallel to each other and engage in holes 70 of the top cover.

FIG. 4 shows a complete drive assembly in a mounted state, including the DC motor 32, the worm drive 52, the transmission unit 54, and an output gear 72, which supports the tape spool 20 and can be directly coupled thereto by a central drive journal. The worm 56 and the worm wheel 58 have rotational axes at 90° to each other. For each full turn of the worm 56, the circumferentially toothed worm wheel 58 advances only one tooth. Given a 22-toothed worm wheel 58, the worm drive 52 will reduce the DC motor speed by the ratio of 22:1. This can be achieved in a considerably smaller volume as compared to plain spur gears. At the same time, the angular position of the gear 60 integral with the worm wheel and ultimately the tape position can be precisely controlled. Moreover, the worm drive 52 has the property that the worm 56 can easily turn the worm wheel 58, but the wheel cannot turn the worm, due to shallow angle of the worm spiral and the greater friction involved. Thus, the direction of transmission is not reversible and the worm drive 52 is self-locking. When the self-locking force exceeds about 10 mNm (milli-Nm) and alternatively about 14 mNm, it is guaranteed for practical purposes that the test tape 22 will be unmovable in the idle mode.

In the transmission unit 54 following the worm drive 52, all spur gears have at least about 14 teeth to ensure a low-noise operation. The rotational axes of the spur gears are parallel to each other and to the axes 74 of the output gear 72 and the tape spool 20, respectively. To achieve a high gear ratio in a limited space, the transmission unit 54 comprises overlapping pairs of stepped wheels 60,62,64. In addition, to reduce the total longitudinal length, the axes 68 of the spur gears 60,62,64,66 are arranged in a non-linear configuration, such that the centers of the spur gears span a trapezoid quadrangle as in the shown arrangement.

For a preferred embodiment, the gear parameters of the gear arrangement 40 are given in the following Table 1, where n is the number of teeth, m is the module, and PD, OD and ID are the pitch diameter, outer diameter and inner diameter (in millimeters), and CC the center to center distance of the spur gears identified by their reference numbers in the first line:

TABLE 1

|    | 56  | 58  | 60   | 62'  | 62'' | 64'  | 64'' | 66  | 72   |
|----|-----|-----|------|------|------|------|------|-----|------|
| n  | 1   | 22  | 14   | 35   | 14   | 26   | 14   | 22  | 60   |
| m  | 0.4 | 0.4 | 0.3  | 0.3  | 0.4  | 0.4  | 0.4  | 0.4 | 0.4  |
| PD | 3.2 | 8.8 | 4.2  | 10.5 | 5.6  | 10.4 | 5.6  | 8.8 | 24   |
| OD | 4   | 9.6 | 4.8  | 11.1 | 6.4  | 11.2 | 6.4  | 9.6 | 24.8 |
| ID | 2.2 | 7.8 | 3.45 | 9.75 | 4.6  | 9.4  | 4.6  | 7.8 | 23   |
| CC |     | 6   |      | 7.35 |      | 8    |      | 7.2 |      |

As can be taken from Table 1, the total gear ratio is 438, thus reducing the DC motor speed in the range of a few thousand rotations per second to an output speed of the output gear of less than 10/s. Due to this high gear ratio, a relatively weak, quiet and compact micro motor 32 can be employed, while an output torque at the output gear 72 of more than 20 mNm still can be achieved.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A hand-held medical device comprising:
a housing with a cassette compartment;
an exchangeable test tape cassette received in the cassette compartment; and
a drive assembly comprising an electric motor and a gear arrangement adapted for rotating a tape spool of the test tape cassette, wherein a test tape of the test tape cassette can be wound forwards and test elements thereon can be provided for successive use, wherein the gear arrangement has a worm drive in which a worm meshes with a worm wheel and a multistage speed-reducing unit comprising a plurality of spur gears arranged between the worm wheel and an output gear directly coupled to the tape spool, wherein each of the plurality of spur gears has at least about 10 teeth, and wherein the worm is directly mounted on a motor shaft of the electric motor.

2. The medical device of claim 1, wherein the multistage speed-reducing unit has at least two meshing gear pairs for reducing rotational speed between the worm drive and the output gear.

3. The medical device of claim 1, wherein the output gear has about 60 teeth, and wherein the electric motor and the output gear have a speed reduction ratio of at least about 300.

4. The medical device of claim 1, wherein the output gear has about 60 teeth, and wherein the electric motor and the output gear have a speed reduction ratio of at least about 400.

5. The medical device of claim 3, wherein the output gear can provide a torque on the tape spool of at least about 20 mNm.

6. The medical device of claim 1, wherein the test tape cassette further comprises a first tape spool for unused tape, a second tape spool for used tape, and a seal through which the test tape is transported between the first spool and the second spool, and where the output gear is acting on the second spool.

7. The medical device of claim 1, wherein the worm drive is self-locking such that the worm wheel cannot drive the worm when a torque is exerted on the tape spool.

8. The medical device of claim 7, wherein the torque exerted on the tape spool is at least about 10 mNm.

9. The medical device of claim 7, wherein the torque exerted on the tape spool is at least about 14 mNm.

10. The medical device of claim 1, wherein rotational axes of the plurality of spur gears are parallel to a rotational axis of the tape spool.

11. The medical device of claim 1, wherein a rotational axis of the electric motor is skewed or perpendicular to rotational axes of the plurality of spur gears.

12. The medical device of claim 1, wherein the plurality of spur gears comprise overlapping pairs of stepped wheels.

13. The medical device of claim 1, wherein the plurality of spur gears are arranged in a non-linear configuration, such that centers of the spur gears span a polygon selected from the group consisting of a triangle and a quadrangle.

14. The medical device of claim 1, wherein the drive assembly is mounted between a top-cover and a bottom-cover of a gearbox.

15. The medical device of claim 14, wherein axes of the plurality of spur gears extend from the bottom-cover to the top-cover of the gearbox, and wherein the shaft of the electric motor lies horizontally between the covers.

16. The medical device of claim 14, wherein the top-cover and the bottom-cover are detachably connected.

17. The medical device of claim 14, wherein the top-cover and the bottom-cover are detachably connected by screws.

18. The medical device of claim 1, wherein the worm wheel has 22 teeth and reduces motor speed by a ratio of 22:1.

19. The medical device of claim 2, wherein the multistage speed-reducing unit has three meshing gear pairs.

20. A hand-held medical device comprising:
a housing with a cassette compartment;
an exchangeable test tape cassette received in the cassette compartment, the test tape cassette comprising a test tape having test elements thereupon that can be provided for successive use and at least one tape spool connected to the test tape; and
a drive assembly comprising an electric motor and a gear arrangement adapted for rotating the tape spool, wherein the gear arrangement has a worm drive in which a worm meshes with a worm wheel and a multistage speed-reducing unit comprising a plurality of spur gears arranged between the worm wheel and an output gear directly coupled to the tape spool, wherein the plurality of spur gears are arranged in a non-linear configuration so that centers of the spur gears span a polygon selected from the group consisting of a triangle and a quadrangle, and wherein a rotational axis of the electric motor is skewed or perpendicular to rotational axes of the plurality of spur gears.

21. The medical device of claim 20, wherein each of the plurality of spur gears has at least about 10 teeth, wherein the output gear has about 60 teeth, and wherein the worm is directly mounted on a motor shaft of the electric motor.

22. The medical device of claim 20, wherein the worm wheel has 22 teeth and reduces motor speed by a ratio of 22:1.

23. The medical device of claim 20, wherein the multistage speed-reducing unit has three meshing gear pairs.

* * * * *